United States Patent [19]

Armand

[11] Patent Number: 5,072,040

[45] Date of Patent: Dec. 10, 1991

[54] PROCESS FOR SYNTHESIS OF SULFONYLIMIDES

[75] Inventor: Michel Armand, S-Martin-d'Uriage, France

[73] Assignees: Centre National de la Recherche Scientifique, Paris, France; Hydro-Quebec, Montreal, Canada

[21] Appl. No.: 613,642

[22] PCT Filed: Apr. 5, 1990

[86] PCT No.: PCT/FR90/00240

§ 371 Date: Dec. 3, 1990

§ 102(e) Date: Dec. 3, 1990

[87] PCT Pub. No.: WO90/11999

PCT Pub. Date: Oct. 18, 1990

[30] Foreign Application Priority Data

Apr. 6, 1989 [FR] France .................. 89 04504

[51] Int. Cl.$^5$ ............................................ C07C 311/15
[52] U.S. Cl. ......................................... 564/82; 564/80
[58] Field of Search ........................................... 564/82

[56] References Cited

U.S. PATENT DOCUMENTS

| | | | |
|---|---|---|---|
| 3,483,208 | 12/1969 | Bahr et al. | 548/542 |
| 4,175,096 | 11/1979 | Reitz et al. | 564/82 |
| 4,505,997 | 3/1985 | Armand et al. | 564/82 |
| 4,697,011 | 9/1987 | DesMarteau | 564/82 |

FOREIGN PATENT DOCUMENTS 1265157  4/1968  Fed. Rep. of Germany ........ 564/82

OTHER PUBLICATIONS

Gordon, Arnold J., et al., "Chemistry of imides, etc", CA 74, 41848d (1971).
Chemical Abstracts, vol. 74, No. 9, Mar. 1, 1971, (Columbus, Ohio, U.S.) A. J. Gordon et al.: "Chemistry of imides, II, Cyclic imides and some unusual products from some diacid chlorides and lithium nitride," p. 312.

*Primary Examiner*—Allen J. Robinson
*Assistant Examiner*—Susan P. Tranor
*Attorney, Agent, or Firm*—Oblon, Spivak, McClelland, Maier & Neustadt

[57] ABSTRACT

The invention relates to a process for the synthesis of sulfonylimides.

The process for the synthesis of sulfonylimides of the general formula $M[RSO_2)_2N]_y$, in which M represents a metal chosen from alkali metals, alkaline earth metals, rare earths, Al, Sc, Y and Th, R represents a monovalent radical chosen from linear or branched aliphatic radicals having 1 to 8 carbon atoms, alicyclic radicals having 3 to 8 carbon atoms, aryl radicals having 3 to 8 carbon atoms, and y is a number equal to the valence of M, is characterized in that an ionic nitride of the formula $M_3N_y$, in which M and y have the meaning given above, is reacted with a sulfonyl halide of the formula $RSO_2X$, in which R has the meaning given above, and X is chosen from F or Cl, in an aprotic polar solvent.

7 Claims, No Drawings

PROCESS FOR SYNTHESIS OF SULFONYLIMIDES

The present invention relates to a process for the synthesis of sulfonylimides and more particularly of symmetrical perfluorosulfonylimides.

The perfluorosulfonylimides of the general formula $M[(R_FSO_2)_2N]_y$, in which M designates a metal or a quaternary or non-quaternary ammonium group, the $R_F$, which are identical in the case of symmetrical imides or different in the case of unsymmetrical imides, represent monovalent perfluorohydrocarbon radicals and especially perfluoroalkyl radicals, such as $CF_3$, $C_2F_5$, $C_4F_9$ or perfluoroaryl radicals, such as $C_6F_5$, and y is a number equal to the valence of M, are of interest, due to the properties connected with the corresponding anion. Indeed, delocalization of the charge of the anion over several electronegative centers, i.e. the F, O and N atoms, induces a weak basicity and a weak nucleophilic character. The stability of the covalent bonds moreover extends the range of redox stability, in particular at anodic potentials. Perfluorosulfonylimides of alkali metals and especially of lithium can be used, in particular, for forming solid solutions with macromolecular materials of the polyether type, the said solid solutions being used as solid polymer electrolytes in the manufacture of primary or secondary thin-film all-solid state generators (U.S. Pat. No. 4,505,997). They are likewise useful as salts in liquid electrolytes.

One of these processes described in EP 96,629 consists, at the very beginning, in reacting the anhydride $(R_FSO_2)_2O$ with urea and a sulfonic acid $R_FSO_3H$ according to the reaction:

$$(R_FSO_2)_2O + R_FSO_3H + OC(NH_2)_2 \rightarrow (R_FSO_2)_2NH$$
$$NH_4CF_3SO_3 + CO_2$$

The products obtained after the reaction are then dissolved in water, and the addition of tetrabutylammonium bromide to the solution obtained precipitates the tetrabutylammonium imide of the formula $(Bu)_4NN(R_FSO_2)_2$.

The sodium imide $NaN(R_FSO_2)_2$ is formed by an ionic exchange reaction between this compound and sodium tetraphenylboron.

The second of these processes consists in reacting the anhydride $(R_FSO_2)_2O$ with pyridine and ammonium chloride according to the reaction scheme:

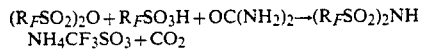

$$NH_4CL + 2(R_FSO_2)_2O + 4C_5H_5N \rightarrow C_5H_5NH$$
$$N(R_FSO_2)_2 + C_2H_5NHCl + 2(C_2H_5NH)CF_3SO_3$$

The reaction products are dissolved in water, and the addition of tetrabutylammonium bromide to the solution obtained leads to the precipitation of tetrabutylammonium imide and then to the salts of other metals as indicated for the first method.

The abovementioned processes are not satisfactory for a large-scale production of the imides, because the overall yields are low and the anhydride precursors $(R_FSO_2)_2O$ are not easily accessible.

The abovementioned imides can also be obtained from the precursors $R_FSO_2F$ by utilizing the four-step synthetic process proposed by J. FOROPOULOS and D. D. DESMARTEAU in the journal INORGANIC CHEMISTRY, Vol. 23 (1984), No. 23, pages 3720 to 3723. In this process, which leads to sodium imide, the reaction scheme is as follows:

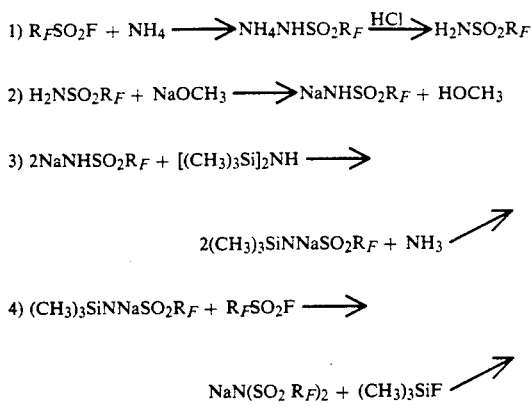

1) $R_FSO_2F + NH_4 \longrightarrow NH_4NHSO_2R_F \xrightarrow{HCl} H_2NSO_2R_F$ 2) $H_2NSO_2R_F + NaOCH_3 \longrightarrow NaNHSO_2R_F + HOCH_3$ 3) $2NaNHSO_2R_F + [(CH_3)_3Si]_2NH \longrightarrow$ $2(CH_3)_3SiNNaSO_2R_F + NH_3 \nearrow$ 4) $(CH_3)_3SiNNaSO_2R_F + R_FSO_2F \longrightarrow$ $NaN(SO_2 R_F)_2 + (CH_3)_3SiF \nearrow$ As for the fourth step of this process, see DE 2,239,817. Apart from a low yield, which is general below 50%, this process cannot be generally applied to precursors of the sulfonyl chloride type $R_FSO_2Cl$, because these compounds do not give, upon reaction with ammonia, the amide $H_2NSO_2R_F$, which is produced in the first step of the method and which is necessary for carrying out the later steps of this method.

Another process consists in obtaining compounds of the N'-substituted N-(amidosulfonyl)sulfonamide type by reacting a sulfonamide with a sulfamoyl chloride.

Another process for the synthesis of sulfonylimides of the formula $M[(RSO_2)_2N]_y$, in which R represents a hydrocarbon radical and more particularly a perfluorohydrocarbon radical $R_F$, and M and y have the meanings given above, was then developed, starting from the corresponding sulfonyl fluorides or chlorides, which are used as precursors. This process consists in reacting a silazane component with a sulfonyl halide component. The silazane component is a silazane or a combination of a silazane derivative with a fluoride having a small lattice energy. The sulfonyl halide component is a sulfonyl fluoride or a combination of sulfonyl chloride with a fluoride of small lattice energy. This process makes it possible to obtain unsymmetrical sulfonylimides in high yields in a single step or in two steps, respectively. However, the silazanes or their derivatives are difficult to handle because they are air-sensitive. Furthermore, they are expensive compounds.

A new process for the synthesis of sulfonylimides from sulfonyl halide and ionic nitrides, which are widely used and easy to handle, has now been found. This process is extremely simple on any scale and uses nitrides, which are low-cost compounds, easy to handle (solids) and easily obtained by direct reaction of the elements (nitrogen + metal).

The invention relates to a process for the synthesis of sulfonylimides of the general formula $M[(RSO_2)_2N]_y$, in which M represents a metal chosen from alkali metals, alkaline earth metals, rare earths, Al, Sc, Y and Th, R represents a monovalent radical chosen from linear or branched aliphatic radicals having 1 to 8 carbon atoms, alicyclic radicals having 3 to 8 carbon atoms, aryl radicals having 3 to 8 carbon atoms, and y is a number equal to the valence of M, characterized in that an ionic nitride of the formula $M_3N_y$, in which M and y have the meaning given above, is reacted with a sulfonyl halide of the formula $RSO_2X$, in which R has the meaning given above, and X is chosen from F or Cl, in an aprotic polar solvent.

The radicals R can contain halogen atoms, for example chlorine or fluorine atoms.

The radicals R having 1 to 4 carbon atoms are of particular interest.

The process is carried out at a temperature between 0° C. and 150° C. In general, a temperature below 40° C. is appropriate.

The process is particularly suited to the preparation of sulfonylimides of alkali metals or alkaline earth metals, in particular of lithium and magnesium.

The reaction proceeds according to the scheme:

$$2yRSO_2X + M_3N_y \rightarrow 2yMX + M[(RSO_2)_2N]_y$$

The ionic nitrides which are suitable for the process of the invention are compounds which contain the moiety $N^{3-}$ and are easily hydrolyzed to give ammonia. Examples of suitable nitrides of this type are alkali metal nitrides, alkaline earth metal nitrides, rare earth nitrides, aluminum nitrides, scandium nitrides, yttrium nitrides and thorium nitrides. The preferred nitrides are alkali metal nitrides and alkaline earth metal nitrides.

The aprotic polar solvents can be chosen from ethers, such as tetrahydrofuran (THF), dimethoxyethane (DME), glymes, amides, such as dimethylformamide (DMF), N-methylpyrrolidone (NMP), tetramethylurea (TMU), dimethylethyleneurea (DMU), tetraethylsulfonamide (TESA), dimethyl sulfoxide (DMSO).

When the sulfonyl halide used for the reaction is a sulfonyl fluoride, the ethers DME and THF, which constitute media which are sufficiently solvating for a rapid reaction to occur are preferably used. When the sulfonyl halide used is a chloride, it is necessary to use solvents which easily donate electron pairs and are of the amide type, in pure form or in the form of mixtures with ethers.

The process of the invention is of particular interest for the synthesis of perfluorinated imides in which the radical R is a perfluoroalkyl or perfluoroaryl radical.

The present invention is described in more detail in the examples which follow and which are given for nonlimiting illustration.

EXAMPLE 1

Preparation of lithium bis(trifluoromethanesulfonyl)imide 304 g of trifluoromethanesulfonyl fluoride are slowly added to a suspension of 35 g of lithium nitride in 500 ml of THF maintained at −18° C. in an autoclave. After sealing the reactor, the mixture is stirred at a temperature of 50° C. until a pressure drop in the reactor is observed. The reaction has taken place according to the following reaction scheme:

$$2CF_3SO_2F + Li_3N \rightarrow Li(CF_3SO_2)_2N + 2<LiF>$$

The lithium fluoride which is insoluble in THF was removed by filtration; the solvent was evaporated to give a solid residue of lithium bis(trifluoromethanesulfonyl)imide. This compound was purified by washing with dichloromethane to give 260 g, which corresponds to a yield of 90%.

EXAMPLE 2

Preparation of lithium bis(perfluorobutanesulfonyl)imide 6.04 g of perfluorobutanesulfonyl fluoride were added to 350 mg of lithium nitride suspended in 20 ml of anhydrous THF. The mixture was stirred at ambient temperature for 48 hours. The reaction took place according to the following reaction scheme:

$$2C_4F_9SO_2F + Li_3N \rightarrow Li(C_4F_9SO_2)_2N + 2<LiF>$$

The imide obtained by the reaction was recovered after filtration to remove the insoluble lithium fluoride formed and evaporation of the solvent. This gave 4.9 g of lithium imide, which corresponds to a yield of 84%.

EXAMPLE 3

Preparation of lithium bis(trifluoromethanesulfonyl)imide 22 ml of trifluoromethanesulfonyl chloride were added to a suspension of 3.5 g of lithium nitride in 100 ml of a mixture of DMF and DME (50/50). The nitride dissolved in a few minutes with stirring at ambient temperature. The reaction took place according to the following reaction scheme:

$$2CF_3SO_2Cl + Li_3N \rightarrow Li(CF_3SO_2)_2N + 2LiCl$$

The solution was filtered, and the filtrate evaporated under reduced pressure. The mixture of lithium chloride and lithium imide was separated by washing with acetonitrile, in which only the imide is soluble, and 26 g of the lithium salt of trifluoromethanesulfonimide were obtained. The yield of imide was 90%.

EXAMPLE 4

Preparation of magnesium bis(trifluoromethanesulfonyl)imide 608 g of trifluoromethanesulfonyl fluoride are added to a suspension of 100 g of magnesium nitride suspended in 500 ml of a mixture of diglyme and TMU (50/50) in an autoclave and cooled to −20° C. After sealing the autoclave, the mixture was maintained at 80° C. for 24 hours. The reaction took place according to the reaction scheme:

$$4CF_3SO_2F + Mg_3N_2 \rightarrow Mg[(CF_3SO_2)_2N]_2 + 2MgF_2$$

The solution obtained was filtered, and the filtrate was then evaporated under reduced pressure. This gave a dry residue comprising 530 g of magnesium imide, which corresponds to a yield of 90.7%.

EXAMPLE 5

Preparation of lithium bis(methanesulfonyl)imide 3.5 g of lithium nitride were added to 23 g of methanesulfonyl chloride $CH_3SO_2Cl$ in 100 ml of DMF. After dissolution of the solid phase, the solvent was evaporated and the dry residue washed with anhydrous THF to remove the lithium chloride formed. The dry residue was extracted with methanol and then dried, to give 14.6 g of $Li(CH_3SO_2)_2N$, which corresponds to a yield of 82%, according to the reaction scheme:

$$2CH_3SO_2Cl + Li_3N \rightarrow 2LiCl + Li(CH_3SO_2)_2N$$

The salts, obtained by carrying out the process according to the invention directly, are stable and isolatable products. From these salts, the corresponding imides can be easily obtained. One possibility is to acidify an aqueous solution of the salt with a strong acid, then to extract the imide formed with a water-immiscible solvent, in particular ethyl ether.

EXAMPLE 6

Preparation of bis(trifluoromethanesulfonyl)imide

The dry residue of the magnesium imide obtained in Example 4 was treated with 200 ml of anhydrous sulfuric acid and distilled under reduced pressure ($2 \times 10^{-3}$ torr at 90° C.). This gave 500 g of pure imide in the form of a hygroscopic solid melting at 30°-35° C.

To prepare a new salt from the imide thus obtained, the imide is reacted with a suitable oxide, hydroxide or carbonate.

Thus, it is possible to prepare from the sulfonylimides easily accessible by the process according to the invention, by simple cation exchange, sulfonylimides which are not accessible by the process, for example because the corresponding nitride does not exist. Of these sulfonylimides, the quaternary ammonium sulfonylimides and especially the tetra-n-butylammonium sulfonylimides may be mentioned.

These compounds, more particularly the trifluoromethanesulfonylimides, are of particular interest in electrochemistry.

EXAMPLE 7

Preparation of a thin polymer/imide film 2.9 g of the compound $Li(CF_3SO_2)_2N$ from Example 1 were dissolved together with 4.4 g of poly(ethylene oxide) of molecular weight $5 \times 10^6$ in 200 ml of acetonitrile. 15 ml of the viscous solution obtained were poured through a glass ring 60 mm in diameter onto a polytetrafluoroethylene plate. After evaporation of the solvent in an oven at 60° C., an elastic and amorphous film of the polymer/salt complex of 220 μm in thickness was obtained. This material has an ionic conductivity of $2 \times 10^{-5}$ (Ωcm) at 25° C. and can be used for the construction of primary or secondary all-solid generators whose negative electrode is composed of metallic lithium or one of its alloys, such as lithium/aluminum.

I claim:

1. Process for the synthesis of sulfonylimides of the general formula $M[(RSO_2)_2N]_y$, in which M represents a metal chosen from alkali metals, alkaline earth metals, rare earths, Al, Sc, Y and Th, R represents a monovalent radical chosen from linear or branched aliphatic radicals having 1 to 8 carbon atoms, alicyclic radicals having 3 to 8 carbon atoms, aryl radicals having 3 to 8 carbon atoms, and y is a number equal to the valence of M, characterized in that an ionic nitride of the formula $M_3N_y$, in which M and y have the meaning given above, is reacted with a sulfonyl halide of the formula $RSO_2X$, in which R has the meaning given above, and X is chosen from F or Cl, in an aprotic polar solvent.

2. Process according to claim 1, characterized in that the radical R is chlorinated or fluorinated.

3. Process according to claim 2, characterized in that R is a perfluoroaryl radical.

4. Process according to any one of claims 1 to 2, characterized in that the radical R contains 1 to 4 carbon atoms.

5. Process according to claim 4, characterized in that R is a perfluoroalkyl radical.

6. Process according to any one of claims 1 to 5, characterized in that M is chosen from alkali metal and alkaline earth metal.

7. Process according to any one of claims 1 to 6, characterized in that the aprotic polar solvent is chosen from ethers, amides, and dimethyl sulfoxide.

* * * * *